US006699479B1

(12) United States Patent
Mebatsion et al.

(10) Patent No.: US 6,699,479 B1
(45) Date of Patent: Mar. 2, 2004

(54) RECOMBINANT NEWCASTLE DISEASE VIRUS AS AN EMBRYO VACCINE

(75) Inventors: Teshome Mebatsion, Boxmeer (NL); Christina Carla Schrier, Boxmeer (NL)

(73) Assignee: Akzo Nobal N.V. (NL)

( * ) Notice: Subject to any disclaimer, the term of this patent is extended or adjusted under 35 U.S.C. 154(b) by 256 days.

(21) Appl. No.: 09/626,223

(22) Filed: Jul. 26, 2000

(30) Foreign Application Priority Data

Jul. 27, 1999 (EP) .............................. 99202467
Mar. 27, 2000 (EP) .............................. 00201091

(51) Int. Cl.$^7$ ....................... A61K 39/17; A61K 39/155; A61K 39/12; C12N 7/01; C12N 7/04; C12N 15/00
(52) U.S. Cl. ................. 424/214.1; 424/204.1; 424/211.1; 435/235.1; 435/236.1; 435/440
(58) Field of Search ............... 424/214.1, 199.1, 424/211.1, 202.1, 204.1, 320.1, 440, 186.1; 536/23.1; 435/440, 236, 235.1

(56) References Cited

U.S. PATENT DOCUMENTS

| 5,427,791 | A | | 6/1995 | Ahmad et al. ............ 424/214.1 |
| 5,733,556 | A | * | 3/1998 | Schrier et al. ............ 424/214.1 |
| 6,410,023 | B1 | * | 6/2002 | Durbin et al. ............ 424/186.1 |

FOREIGN PATENT DOCUMENTS

| EP | 0 760 394 A1 | 3/1979 |
| EP | 0 848 956 A1 | 6/1998 |
| WO | WO 99/66045 | 12/1999 |

OTHER PUBLICATIONS

Fields et al. Virology, vol. 1, 3rd edition. 1995. Philadelphia: Lippencott Williams & Wilkins. Figure 6, p. 1212.*
Kato et al. The EMBO Journal. 1997; 16 (3): 578–587.*
Gagic et al. Avian Diseases. 1999; 43: 293–301.*
Stone et al., "In Ovo Vaccination of Chicken Embryos with Experimental Newcastle Disease and Avian Influenza Oil–Emulsion Vaccines," Avian Diseases, 1997, vol. 41, pp. 856–863.
Kato et al., "Importance of the Cysteine–Rich Carboxyl–Terminal Half of V Protein for Sendai Virus Pathogenesis," Journal of Virology, 1997, vol. 71, No. 10, pp. 7266–7272.
Peeters et al., "Rescue of Newcastle Disease Virus from Cloned cDNA: Evidence that Cleavability of the Fusion Protein is a Major Determinant for Virulence," Journal of Virology, 1999, vol. 73, No. 6, pp. 5001–5009.
Steward et al., "RNA Editing in Newcastle Disease Virus," Journal of General Virology, 1993, vol. 74, pp. 2539–2547.

* cited by examiner

Primary Examiner—Mary E. Mosher
Assistant Examiner—Shanon Foley
(74) Attorney, Agent, or Firm—Mark W. Milstead

(57) ABSTRACT

The present invention provides a NDV mutant which is suited as vaccine candidate for in ovo vaccination. The mutant expresses reduced levels of V protein and can safely be administered to chicken embryos before hatch.

17 Claims, 2 Drawing Sheets

Figure 2

AF  rNDV  P1          AF  rNDV  P1

NP▶

◀V 1   2   3            4   5   6

SEQUENCE LISTING

```
<160> NUMBER OF SEQ ID NOS: 46

<210> SEQ ID NO 1
<211> LENGTH: 27
<212> TYPE: DNA
<213> ORGANISM: PARAMYXOVIRIDAE
<220> FEATURE:
<221> NAME/KEY: CDS
<222> LOCATION: (1)..(27)
<223> OTHER INFORMATION: FlNDV

<400> SEQUENCE: 1 aat gct aaa aag ggc cca tgg tcg agc                                    27
Asn Ala Lys Lys Gly Pro Trp Ser Ser
1               5

<210> SEQ ID NO 2
<211> LENGTH: 9
<212> TYPE: PRT
<213> ORGANISM: PARAMYXOVIRIDAE

<400> SEQUENCE: 2

Asn Ala Lys Lys Gly Pro Trp Ser Ser
1               5

<210> SEQ ID NO 3
<211> LENGTH: 28
<212> TYPE: DNA
<213> ORGANISM: PARAMYXOVIRIDAE
<220> FEATURE:
<221> NAME/KEY: CDS
<222> LOCATION: (1)..(27)
<223> OTHER INFORMATION: FlNDV

<400> SEQUENCE: 3 aat gct aaa aag ggg ccc atg gtc gag c                                  28
Asn Ala Lys Lys Gly Pro Met Val Glu
1               5

<210> SEQ ID NO 4
<211> LENGTH: 9
<212> TYPE: PRT
<213> ORGANISM: PARAMYXOVIRIDAE

<400> SEQUENCE: 4

Asn Ala Lys Lys Gly Pro Met Val Glu
1               5

<210> SEQ ID NO 5
<211> LENGTH: 27
```

```
<212> TYPE: DNA
<213> ORGANISM: PARAMYXOVIRIDAE
<220> FEATURE:
<221> NAME/KEY: CDS
<222> LOCATION: (1)..(27)
<223> OTHER INFORMATION: P1 - P ORF

<400> SEQUENCE: 5 aat gct aag aag ggc cca tgg tcg agc                                27
Asn Ala Lys Lys Gly Pro Trp Ser Ser
1               5

<210> SEQ ID NO 6
<211> LENGTH: 9
<212> TYPE: PRT
<213> ORGANISM: PARAMYXOVIRIDAE

<400> SEQUENCE: 6

Asn Ala Lys Lys Gly Pro Trp Ser Ser
1               5

<210> SEQ ID NO 7
<211> LENGTH: 27
<212> TYPE: DNA
<213> ORGANISM: PARAMYXOVIRIDAE
<220> FEATURE:
<221> NAME/KEY: CDS
<222> LOCATION: (1)..(27)
<223> OTHER INFORMATION: PCG12 - P ORF

<400> SEQUENCE: 7 aat gct cga aag ggc cca tgg tcg agc                                27
Asn Ala Arg Lys Gly Pro Trp Ser Ser
1               5

<210> SEQ ID NO 8
<211> LENGTH: 9
<212> TYPE: PRT
<213> ORGANISM: PARAMYXOVIRIDAE

<400> SEQUENCE: 8

Asn Ala Arg Lys Gly Pro Trp Ser Ser
1               5

<210> SEQ ID NO 9
<211> LENGTH: 27
<212> TYPE: DNA
<213> ORGANISM: PARAMYXOVIRIDAE
<220> FEATURE:
<221> NAME/KEY: CDS
<222> LOCATION: (1)..(27)
<223> OTHER INFORMATION: PG2 - P ORF

<400> SEQUENCE: 9 aat gct aga aag ggc cca tgg tcg agc                                27
Asn Ala Arg Lys Gly Pro Trp Ser Ser
1               5

<210> SEQ ID NO 10
<211> LENGTH: 9
<212> TYPE: PRT
<213> ORGANISM: PARAMYXOVIRIDAE

<400> SEQUENCE: 10

Asn Ala Arg Lys Gly Pro Trp Ser Ser
1               5
```

```
<210> SEQ ID NO 11
<211> LENGTH: 27
<212> TYPE: DNA
<213> ORGANISM: PARAMYXOVIRIDAE
<220> FEATURE:
<221> NAME/KEY: CDS
<222> LOCATION: (1)..(27)
<223> OTHER INFORMATION: PC4 - P ORF

<400> SEQUENCE: 11 aat gct aaa cag ggc cca tgg tcg agc                              27
Asn Ala Lys Gln Gly Pro Trp Ser Ser
1               5

<210> SEQ ID NO 12
<211> LENGTH: 9
<212> TYPE: PRT
<213> ORGANISM: PARAMYXOVIRIDAE

<400> SEQUENCE: 12

Asn Ala Lys Gln Gly Pro Trp Ser Ser
1               5

<210> SEQ ID NO 13
<211> LENGTH: 27
<212> TYPE: DNA
<213> ORGANISM: PARAMYXOVIRIDAE
<220> FEATURE:
<221> NAME/KEY: CDS
<222> LOCATION: (1)..(27)
<223> OTHER INFORMATION: PG5 - P ORF

<400> SEQUENCE: 13 aat gct aaa agg ggc cca tgg tcg agc                              27
Asn Ala Lys Arg Gly Pro Trp Ser Ser
1               5

<210> SEQ ID NO 14
<211> LENGTH: 9
<212> TYPE: PRT
<213> ORGANISM: PARAMYXOVIRIDAE

<400> SEQUENCE: 14

Asn Ala Lys Arg Gly Pro Trp Ser Ser
1               5

<210> SEQ ID NO 15
<211> LENGTH: 27
<212> TYPE: DNA
<213> ORGANISM: PARAMYXOVIRIDAE
<220> FEATURE:
<221> NAME/KEY: CDS
<222> LOCATION: (1)..(27)
<223> OTHER INFORMATION: PA - P ORF

<400> SEQUENCE: 15 aat gct gcg aag ggc cca tgg tcg agc                              27
Asn Ala Ala Lys Gly Pro Trp Ser Ser
1               5

<210> SEQ ID NO 16
<211> LENGTH: 9
<212> TYPE: PRT
<213> ORGANISM: PARAMYXOVIRIDAE

<400> SEQUENCE: 16

Asn Ala Ala Lys Gly Pro Trp Ser Ser
1               5
```

```
<210> SEQ ID NO 17
<211> LENGTH: 27
<212> TYPE: DNA
<213> ORGANISM: PARAMYXOVIRIDAE
<220> FEATURE:
<221> NAME/KEY: CDS
<222> LOCATION: (1)..(27)
<223> OTHER INFORMATION: PD - P ORF

<400> SEQUENCE: 17 aat gct gac aag ggc cca tgg tcg agc                                    27
Asn Ala Asp Lys Gly Pro Trp Ser Ser
1               5

<210> SEQ ID NO 18
<211> LENGTH: 9
<212> TYPE: PRT
<213> ORGANISM: PARAMYXOVIRIDAE

<400> SEQUENCE: 18

Asn Ala Asp Lys Gly Pro Trp Ser Ser
1               5

<210> SEQ ID NO 19
<211> LENGTH: 27
<212> TYPE: DNA
<213> ORGANISM: PARAMYXOVIRIDAE

-continued

Asn Ala Arg Arg Gly Pro Trp Ser Ser
1               5

<210> SEQ ID NO 23
<211> LENGTH: 21
<212> TYPE: DNA
<213> ORGANISM: PARAMYXOVIRIDAE
<220> FEATURE:
<221> NAME/KEY: CDS
<222> LOCATION: (1)..(21)
<223> OTHER INFORMATION: delta 6 - P ORF

<400> SEQUENCE: 23 aat gct ggc cca tgg tcg agc                                          21
Asn Ala Gly Pro Trp Ser Ser
1               5

<210> SEQ ID NO 24
<211> LENGTH: 7
<212> TYPE: PRT
<213> ORGANISM: PARAMYXOVIRIDAE

<400> SEQUENCE: 24

Asn Ala Gly Pro Trp Ser Ser
1               5

<210> SEQ ID NO 25
<211> LENGTH: 15
<212> TYPE: DNA
<213> ORGANISM: PARAMYXOVIRIDAE
<220> FEATURE:
<221> NAME/KEY: CDS
<222> LOCATION: (1)..(15)
<223> OTHER INFORMATION: delta 12 - P ORF

<400> SEQUENCE: 25 ggc cca tgg tcg agc                                                  15
Gly Pro Trp Ser Ser
1               5

<210> SEQ ID NO 26
<211> LENGTH: 5
<212> TYPE: PRT
<213> ORGANISM: PARAMYXOVIRIDAE

<400> SEQUENCE: 26

Gly Pro Trp Ser Ser
1               5

<210> SEQ ID NO 27
<211> LENGTH: 27
<212> TYPE: DNA
<213> ORGANISM: PARAMYXOVIRIDAE
<220> FEATURE:
<221> NAME/KEY: CDS
<222> LOCATION: (1)..(27)
<223> OTHER INFORMATION: Vstop - P ORF

<400> SEQUENCE: 27 aat gct aaa aag ggc cca tgg tct agc                                  27
Asn Ala Lys Lys Gly Pro Trp Ser Ser
1               5

<210> SEQ ID NO 28
<211> LENGTH: 9
<212> TYPE: PRT
<213> ORGANISM: PARAMYXOVIRIDAE

-continued

<400> SEQUENCE: 28

Asn Ala Lys Lys Gly Pro Trp Ser Ser
1               5

<210> SEQ ID NO 29
<211> LENGTH: 27
<212> TYPE: DNA
<213> ORGANISM: PARAMYXOVIRIDAE
<220> FEATURE:
<221> NAME/KEY: CDS
<222> LOCATION: (1)..(27)
<223> OTHER INFORMATION: Vstop - P ORF

<400> SEQUENCE: 29 aat gct aaa aag ggg ccc atg gtc tag                         27
Asn Ala Lys Lys Gly Pro Met Val
1               5

<210> SEQ ID NO 30
<211> LENGTH: 8
<212> TYPE: PRT
<213> ORGANISM: PARAMYXOVIRIDAE

<400> SEQUENCE: 30

Asn Ala Lys Lys Gly Pro Met Val
1               5

<210> SEQ ID NO 31
<211> LENGTH: 26
<212> TYPE: DNA
<213> ORGANISM: PARAMYXOVIRIDAE
<220> FEATURE:
<221> NAME/KEY: misc_feature
<222> LOCATION: (1)..(26)
<223> OTHER INFORMATION: primer P1

<400> SEQUENCE: 31
ccatgggccc ttcttagcat tggacg                                26

<210> SEQ ID NO 32
<211> LENGTH: 26
<212> TYPE: DNA
<213> ORGANISM: PARAMYXOVIRIDAE
<220> FEATURE:
<221> NAME/KEY: misc_feature
<222> LOCATION: (1)..(26)
<223> OTHER INFORMATION: primer PCG12

<400> SEQUENCE: 32
ccatgggccc tttcgagcat tggacg                                26

<210> SEQ ID NO 33
<211> LENGTH: 26
<212> TYPE: DNA
<213> ORGANISM: PARAMYXOVIRIDAE
<220> FEATURE:
<221> NAME/KEY: misc_feature
<222> LOCATION: (1)..(26)
<223> OTHER INFORMATION: primer PG2

<400> SEQUENCE: 33
ccatgggccc tttctagcat tggacg                                26

<210> SEQ ID NO 34
<211> LENGTH: 26
<212> TYPE: DNA
<213> ORGANISM: PARAMYXOVIRIDAE

<220> FEATURE:
<221> NAME/KEY: misc_feature
<222> LOCATION: (1)..(26)
<223> OTHER INFORMATION: primer PC4

<400> SEQUENCE: 34
ccatgggccc tgtttagcat tggacg                                    26

<210> SEQ ID NO 35
<211> LENGTH: 26
<212> TYPE: DNA
<213> ORGANISM: PARAMYXOVIRIDAE
<220> FEATURE:
<221> NAME/KEY: misc_feature
<222> LOCATION: (1)..(26)
<223> OTHER INFORMATION: primer PG5

<400> SEQUENCE: 35
ccatgggccc cttttagcat tggacg                                    26

<210> SEQ ID NO 36
<211> LENGTH: 26
<212> TYPE: DNA
<213> ORGANISM: PARAMYXOVIRIDAE
<220> FEATURE:
<221> NAME/KEY: misc_feature
<222> LOCATION: (1)..(26)
<223> OTHER INFORMATION: primer PA

<400> SEQUENCE: 36
ccatgggccc ttcgcagcat tggacg                                    26

<210> SEQ ID NO 37
<211> LENGTH: 26
<212> TYPE: DNA
<213> ORGANISM: PARAMYXOVIRIDAE
<220> FEATURE:
<221> NAME/KEY: misc_feature
<222> LOCATION: (1)..(26)
<223> OTHER INFORMATION: primer PD

<400> SEQUENCE: 37
ccatgggccc ttgtcagcat tggacg                                    26

<210> SEQ ID NO 38
<211> LENGTH: 26
<212> TYPE: DNA
<213> ORGANISM: PARAMYXOVIRIDAE
<220> FEATURE:
<221> NAME/KEY: misc_feature
<222> LOCATION: (1)..(26)
<223> OTHER INFORMATION: primer PR

<400> SEQUENCE: 38
ccatgggccc ttgcgagcat tggacg                                    26

<210> SEQ ID NO 39
<211> LENGTH: 26
<212> TYPE: DNA
<213> ORGANISM: PARAMYXOVIRIDAE
<220> FEATURE:
<221> NAME/KEY: misc_feature
<222> LOCATION: (1)..(26)
<223> OTHER INFORMATION: primer PRR

<400> SEQUENCE: 39
ccatgggccc cggcgagcat tggacg                                    26

```
<210> SEQ ID NO 40
<211> LENGTH: 20
<212> TYPE: DNA
<213> ORGANISM: PARAMYXOVIRIDAE
<220> FEATURE:
<221> NAME/KEY: misc_feature
<222> LOCATION: (1)..(20)
<223> OTHER INFORMATION: primer delta 6

<400> SEQUENCE: 40
ccatgggcca gcattggacg                                              20

<210> SEQ ID NO 41
<211> LENGTH: 27
<212> TYPE: DNA
<213> ORGANISM: PARAMYXOVIRIDAE
<220> FEATURE:
<221> NAME/KEY: misc_feature
<222> LOCATION: (1)..(27)
<223> OTHER INFORMATION: primer delta 12

<400> SEQUENCE: 41
ccatgggccg gacgatttat tgctgag                                      27

<210> SEQ ID NO 42
<211> LENGTH: 27
<212> TYPE: DNA
<213> ORGANISM: PARAMYXOVIRIDAE
<220> FEATURE:
<221> NAME/KEY: misc_feature
<222> LOCATION: (1)..(27)
<223> OTHER INFORMATION: primer Vstop

<400> SEQUENCE: 42
aagggcccat ggtctagccc ccaagag                                      27

<210> SEQ ID NO 43
<211> LENGTH: 21
<212> TYPE: DNA
<213> ORGANISM: PARAMYXOVIRIDAE
<220> FEATURE:
<221> NAME/KEY: misc_feature
<222> LOCATION: (1)..(21)
<223> OTHER INFORMATION: primer FWP#4

<400> SEQUENCE: 43
gctcctcgcg gctcagactc g                                            21

<210> SEQ ID NO 44
<211> LENGTH: 21
<212> TYPE: DNA
<213> ORGANISM: PARAMYXOVIRIDAE
<220> FEATURE:
<221> NAME/KEY: misc_feature
<222> LOCATION: (1)..(21)
<223> OTHER INFORMATION: primer RP#20

<400> SEQUENCE: 44
cccgggaatc ttctctggcg c                                            21

<210> SEQ ID NO 45
<211> LENGTH: 21
<212> TYPE: DNA
<213> ORGANISM: PARAMYXOVIRIDAE
<220> FEATURE:
<221> NAME/KEY: misc_feature
<222> LOCATION: (1)..(21)
<223> OTHER INFORMATION: primer P#13
```

```
<400> SEQUENCE: 45
ccacccaggc cacagacgaa g                                          21

<210> SEQ ID NO 46
<211> LENGTH: 18
<212> TYPE: DNA
<213> ORGANISM: PARAMYXOVIRIDAE
<220> FEATURE:
<221> NAME/KEY: misc_feature
<222> LOCATION: (1)..(18)
<223> OTHER INFORMATION: primer P#17

<400> SEQUENCE: 46
atgaattcag ctgttgga                                              18
```

RECOMBINANT NEWCASTLE DISEASE VIRUS AS AN EMBRYO VACCINE

Figure 1:
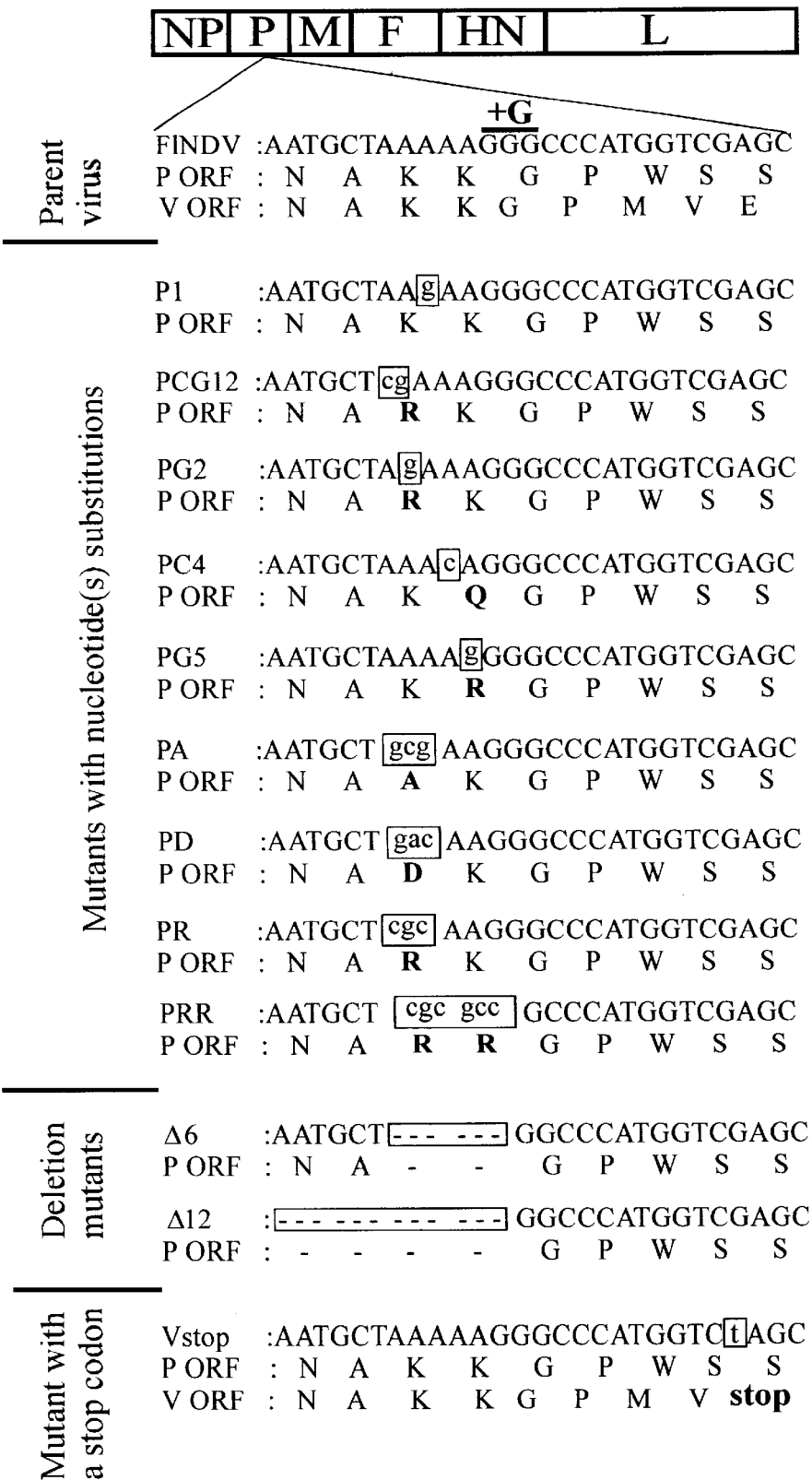

The present invention is concerned with a Newcastle disease virus (NDV) mutant that expresses its V protein at a reduced level, a vaccine comprising the NDV mutant and the use of the NDV mutant for the manufacture of a vaccine to protect birds against ND Newcastle disease (ND) is one of the devastating diseases of poultry and has substantial economic impact on the poultry industry. NDV is the etiologic agent of this disease and belongs to the family Paramyxoviridae. Newcastle disease is complicated in that different isolates and strains of the virus may induce substantial variation in the severity of the disease. In general, the younger the chicken the more acute and severe the disease. The infection may take place by either inhalation or ingestion of the virus. The infectious form of the virus spreads from one bird to another.

In order to reduce the economic losses due to ND in the poultry industry, vaccination of chickens, particularly those raised for commercial consumption, is carried out throughout the world on a routine basis. Examples of live (lentogenic) NDV vaccine strains commonly used are the V4, Hitchner B 1, F and La Sota strain. However, these vaccine strains still cause light to moderate vaccination reactions, in particular in the respiratory tract upon primary vaccination of young birds.

Mild NDV vaccine strains have been developed which do not cause (respiratory) vaccination reactions upon administration to young birds: U.S. Pat. No. 5,250,298 (University of Delaware) discloses a live, cold-adapted temperature-sensitive mutant of the Hitchner B1 strain, designated as CaTs. U.S. Pat. No. 5,149,530 (Duphar Int. Res. B.V.) describes a NDV strain, designated as NDW, which is a mutant derived from the Ulster 2C strain. U.S. Pat. No. 5,750,111 (Akzo Nobel N.V.) discloses a mild vaccine strain, designated as the C2 strain, which does not induce adverse reactions in one-day-old chicks.

Currently available NDV vaccines can only be administered to hatched chickens through drinking water, aerosol, eye drops or by parenteral routes. These methods of applications have some disadvantages, most importantly expensive because of the labour needed for their application. Recently, the use of vaccines, such as herpesvirus of turkey and infectious bursal disease virus vaccines as embryo vaccines (Sharma and Burmester, Avian Diseases 26, 134–149, 1982 and Sharma, Avian Diseases 29, 1155–1169, 1985) has proved to be effective and economical. Moreover, embryo vaccination was found to be advantageous due to early age of resistance to the specific disease and administration of a uniform dose of vaccine into each egg using semiautomatic machines with multiple injection heads.

It should be noted that many vaccines used conventionally for post-hatch vaccination of birds cannot be used for in ovo vaccination. Late stage embryos are highly susceptible to infection with most vaccine viruses examined, including those vaccine viruses which can safely be used in one-day-old hatched chicks. Consequently, conventional vaccines must be modified for in ovo use.

Currently, there is no suitable commercially available ND vaccine that can be applied in ovo, mainly due to high level of embryo mortality associated even with two of the mildest commercially available NDV vaccine strains: NDW and C2. U.S. Pat. No. 5,427,791 (Regents of the University of Minnesota) discloses the use of chemical mutagenic agents to produce NDV mutants of the Hitchner BI strain that are non-pathogenic for late stage embryos. Chemical treatment of the BI strain with ethyl methanine sulfonate (EMS) resulted in the mutant virus NDV-B1-EMS which could be safely administered to chicken eggs at embryonation day 18. However, such mutagenic process leads to the introduction of random mutations in the genome of the virus in an uncontrolled, non-reproducible way. Such random mutations may influence properties of the virus other than those associated with the safety in ovo, such as properties of the virus related to the immunogenicity. Moreover, disadvantageously, each egg passage step of this strain must be carried out in the presence of the mutagenic agent EMS because of the property of the mutant to revert back to the parent B1 strain which is not safe for embryos.

Recently, genetic modification of non-segmented negative stranded RNA viruses has become possible by the development of a process referred to as "reverse genetics" (reviewed in Conzelmann, J. Gen. Virology 77, 381–389, 1996; Conzelmann, Annu. Rev. Genet. 32, 123–162, 1998 and Palese et al., Proc. Natl. Acad. Sci. 93, 11354–11358, 1996). The established reverse genetics system that enable controlled genetic manipulation of negative strand RNA viruses has potential applications for the development of novel vaccine strains.

NDV is a member of the family Paramyxoviridae and its negative-strand RNA virus genome contains six genes encoding six major structural proteins (3'NP-P-M-F-HN-L 5'). A general feature of paramyxoviruses, however, is the presence of additional structural or non-structural viral proteins resulting from the use of alternative reading frames and RNA editing of their P gene (reviewed by Kolakofsky et al., J. Virology 72, 891–899, 1998). Like other paramyxoviruses, NDV is also found to edit its P gene by inserting one or two G residues at the editing locus (UUUUCCC). The three mRNAs encode the P protein (unedited), the V ORF (with +1 frame-shift) and the W ORF (with +2 frame-shift) (Steward et al., J. Gen. Virology 74, 2539–2547, 1993). Translation of the P, V and W specific mRNAs result in the expression of three proteins which have the same N-terminal halve but which differ in their C-terminal halves as a result of the use of different reading frames down-stream of the editing locus.

Peeters et al. (J. Virology 73, 5001–5009, 1999) and R ömer-Oberdörfer et al. (J. Gen. Virol. 80, 2987–2995, 1999) described the generation of infectious NDV entirely from cloned cDNA by the reverse genetics system. It is shown in Peeters et al (1999) that the virulence of a NDV vaccine strain can be increased dramatically by modifying the amino acid sequence at the cleavage site of the $F_0$ protein. It is also suggested that that elimination of expression of the V protein of NDV may result in an attenuated phenotype in birds (Peeters et al., 1999, supra).

It is an object of the present invention to identify a NDV mutant which can be used for the manufacture of a vaccine for the protection of birds against ND which can be administered not only to young birds after hatch, but which can also be administered safely in ovo.

A new NDV mutant has been identified herein that displays not only mild, attenuated properties for young hatched chickens similar to those displayed by the commercially available mild NDW and C2 vaccine strains, but which in contrast to the NDW and C2 vaccine strains, can also safely be used for embryo vaccination.

The invention provides a NDV mutant that expresses its V protein at a reduced level (NDV V⁻), characterised in that the mutant is phenotypically V protein positive and wherein ≦6% of its P-gene derived mRNAs in infected cells encode V ORF.

It has been found that a NDV mutant as defined above causes significantly less embryo mortality, even if administered to embryos at 11 days of age. This is in contrast to the parent lentogenic vaccine strain from which the mutant is derived. This vaccine strain kills all the embryos before they hatch. Additionally, it was found that a NDV V⁻ mutant does not affect hatchability of the eggs, particularly of embryonated commercial chicken eggs and that chickens hatched from embryo vaccinated eggs were protected against virulent NDV challenge. These unexpected combined properties of a NDV V⁻ mutant make such a mutant especially suitable for the manufacture of a vaccine for in ovo administration.

Surprisingly, it has been found that NDV mutants that are not able to express V protein generated by reverse genetics techniques can not be rescued after passage of transfection supernatants into embryonated chicken eggs. The complete elimination of V protein expression of a NDV mutant does not result in infectious virus particles and, hence, should be prevented.

Therefore, a NDV mutant according to the invention is phenotypical positive but immunological tests demonstrate that the level of V protein produced in an infected cell is reduced when compared with a cell infected with the parent NDV. The presence or absence (the phenotype) and relative level of V protein expression in an infected host cell can be determined in an immune fluorescence test (IFT) or immunoblotting using a specific V protein antiserum raised against the C-terminus of the V protein as described herein.

A NDV V⁻ mutant according to the invention clearly displays defective P-gene mRNA editing. Compared to cells infected with the parent NDV in which the P-gene derived mRNAs encoding V ORF (and W ORF) are generally present at a frequency of approximately 30% (and 2%), a NDV V⁻ mutant according to the invention edits its P gene at a frequency of only $\leq 6\%$.

The relative occurrence of the P-gene derived mRNA populations can be determined as described in Example 1. In this respect, the number of clones used for the determination of the P-gene mRNA editing frequency should be at least 100, preferably between 100 and 500. For a phenotypical V protein positive NDV V⁻ mutant, V ORF editing is higher than 0%.

Preferably, the phenotypical V protein positive NDV V⁻ mutant is a mutant wherein $\leq 3\%$ and more preferably $\leq 1\%$ of its P-gene derived mRNAs in infected cells encode V ORF.

Alternatively, a NDV V⁻ according to the invention can also be defined by means of the level of its V ORF editing frequency: the NDV V⁻ mutant according to the invention displays a percentage V ORF editing frequency (e.f.) of 0 <e.f. $\leq 6$, preferably 0 <e.f. $\leq 3$, more preferably 0 <e.f $\leq 1$.

The NDV V⁻ mutant can be used for the manufacture of a ND vaccine for in ovo administration according to standard methods as commonly used for the preparation of conventional live ND vaccines.

Briefly, a susceptible substrate is inoculated with a NDV V⁻ mutant and propagated until the virus replicated to a desired titre after which NDV containing material is harvested. Subsequently, the harvested material is formulated into a pharmaceutical preparation with immunising properties.

Every substrate which is able to support the replication of ND viruses can be used in the present invention, including primary (avian) cell cultures, such as chicken embryo fibroblast cells (CEF) or chicken kidney cells (CK), or mammalian cell lines such as the VERO cell line or baby hamster kidney (BHK) cell line.

Particularly suited substrates on which the NDV V⁻ mutant can be propagated are SPF embryonated eggs. Embryonated eggs can be inoculated with, for example 0.2 ml NDV containing allantoic fluid comprising at least $10^{2.0}$ $EID_{50}$ per egg. Preferably, 9–12 day-old embryonated eggs are inoculated with about $10^{5.0}$ $EID_{50}$ and subsequently incubated at 37° C. for 2–4 days. After 2–4 days the ND virus product can be harvested preferably by collecting the allantoic fluid. The fluid can be centrifuged thereafter for 10 min. at 2500 g followed by filtering the supernatant through a filter (100 μm).

The vaccine to be used for the in ovo administration comprises the live ND virus mutant and a pharmaceutically acceptable carrier or diluent customary used for such compositions. The vaccine can be prepared and marketed in the form of a suspension or in a lyophilised form. Carriers include stabilisers, preservatives and buffers. Suitable stabilisers are, for example SPGA, carbohydrates (such as sorbitol, mannitol, starch, sucrose, dextran, glutamate or glucose), proteins (such as dried milk serum, albumin or casein) or degradation products thereof. Suitable buffers are for example alkali metal phosphates. Suitable preservatives are thimerosal, merthiolate and gentamicin. Diluents include water, aqueous buffer (such as buffered saline) and polyols (such as glycerol).

The vaccine comprising the NDV V⁻ mutant can be injected into embryonated eggs according to conventional in ovo vaccination methods. Usually, the vaccine is injected into embryonated eggs during late stages of the embryonation, generally during the final quarter of the incubation period (day 15–21), preferably at day 18 of the incubation period.

The mechanism of injection of the incubated eggs is not particularly critical provided that it does not unduly damage tissue and organs of the embryo. For example, a small hole is pierced with a needle (11½ inch, about 22 gauge) attached to syringe in the large end of the shell and the vaccine is injected below the inner shell membrane and the chorioallantoic membrane. Subsequently, the vaccinated embryonated eggs are transferred to an incubator to hatch (U.S. Pat. No. 4,458,630, 5,427,791, WO 98/56413 and WO 95/35121). Preferably, the whole embryo vaccination process is carried out using automated vaccination systems, such as the commercially available Inovoject®.

The NDV V⁻ mutant used for the manufacture of the ND vaccine for in ovo administration can be prepared according to the established reverse genetics method which has already been used for the genetic modification of many non-segmented, negative stranded RNA viruses (for reviews see above). Additionally, such a method has also been disclosed for NDV by Peeters et al. (1999, supra) and Römer-Oberdörfer et al. (1999, supra).

Typically, first, a full length cDNA clone of the NDV genome is assembled (from overlapping cDNA fragments) and cloned into a transcription plasmid between a (T7) RNA polymerase promoter and an autocatalytic hepatitis delta virus ribozyme. Transfection of this plasmid into cells that express a (T7) RNA polymerase results in the synthesis of antigenome NDV RNA. Simultaneous expression from co-transfected plasmids of the viral proteins that are required for virus replication and transcription (NP, P and L proteins) result in the generation of infectious virus from cloned cDNA. The nucleotide sequences of all NDV genes are known. The nucleotide sequence of the P gene have been described by Ishida et al., NAR 14, 6551–6564, 1986; McGinnes et al., Virology 164, 256–264, 1988; Daskalakis et al., NAR 20, 616, 1992 and Steward et al., J. Gen.

Virology 74, 2539–2547, 1993). The nucleotide sequence of the complete NDV genome has also been reported by several research groups (de Leeuw et al., J. Gen. Virology 80, 131–136, 1999, GenBank accession no. AF077761; Krishnamurthy et al., J. Gen Virology 79, 2419–2424, 1998, Phillips et al., Arch. Virol. 143, 1993–2002, 1998, EMBL accession no. AJ225127, AJ225128 and AJ225129 and Romer-Oberdorfer et al., J. Gen. Virol. 80, 2987–2995, 1999; EMBL accession no. Y18898). The length of the complete NDV genome is 15,186 nucleotides including the 3'- and 5'- terminal ends.

The P gene is located on the NDV genome at nucleotides 1804–3254 (NDV strain Clone 30® numbering as used by Romer-Oberdorfer et al., EMBL accession no. Y18898; this numbering will be used herein to identify positions on the NDV genome). The open reading frame (ORF) encoding the P protein is located at nucleotides 1887–3074. The P gene mRNA editing locus UUU UUC CC (genome RNA-sense) to be mutated resulting in a NDV V$^-$ mutant is located at position 2280–2287. The end of the ORFs encoding the P, V and W protein are at positions 3074 (TAA), 2605 (TAA) and 2424 (TGA), respectively. The P protein is 395 amino acids long and the N-terminal halve of the P protein which is identical to the N-terminal halve of the V protein (and W protein) extends from amino acid 1–135. The C-terminal halves of the P and V proteins, i.e. the fragments of the P and V protein that share no sequence homology, extend from amino acid 136–395 and 136–239, respectively. Because of the (+1) frame-shift at the end of the editing locus during transcription, the C-terminal halves of the P- and V protein do not show any similarity.

Preferably, the present invention provides a NDV V$^-$ mutant that expresses its V protein at a reduced level as a result of a mutation in the editing locus UUU UUC CC. The disturbance of this highly specific sequence results in a reduction of the insertion frequency of non-templated G residue(s) at the editing site during transcription and, consequently, in a reduction of V (and W) protein expression.

A mutation is understood to be a change of the genetic information in the editing locus of the P gene of a parent NDV strain which is able to express a V protein. The mutation is, in particular, a nucleic acid substitution.

In particular, a nucleic acid substitution is introduced in one of the codons of the editing locus which results in a silent mutation, i.e. a mutation which alters the codon but not the amino acid encoded by that codon. Such a mutation guarantees that the ORF of the P gene still expresses a functional P protein. Examples of silent mutations at the conserved editing site including a mutation at position 3 (UUC UUC CC) or position 6 (UUU UUU CC) or a combination of both mutations (UUC UUU CC) are within the scope of this invention.

As demonstrated in Example 1, substitutions of 3 or more nucleotides and deletions of nucleotides result in NDV mutants that are not able to express V protein and can not be rescued from the transfection supernatants. Therefore, the substitution in the editing locus of a NDV mutant according to the invention comprises 1 or 2 nucleotides. Furthermore, it is demonstrated in Example 1 that mutations introduced at position 1–5 involving 1 or 2 nucleotides of the editing locus advantageously result in a NDV mutant that can be rescued from transfection supernatants and displays a reduced V expression of approximately 20-fold lower than that of the parent virus. Moreover, all the mutants are considerably attenuated in pathogenicity for chicken embryos. In view of these findings, a NDV mutant as described above having 1 or 2 mutations at position 1–5 of the editing locus, preferably at postion 3 or 4 is specifically contemplated.

A very advantageous example of a NDV V$^-$ mutant according to the invention having a mutation at position 3 of the editing locus comprises the nucleotide sequence UUC UUC CC at the editing locus. Although the first codon of the editing locus of this mutant is changed, the amino acid encoded by this codon remains the same (a lysine residue). This NDV V$^-$ mutant dramatically reduces P gene mRNA editing as demonstrated by the reduction (to ≦6%) of V (and W to undetectable levels) ORF mRNAs. NDV V$^-$ mutants demonstrating a similar reduction of V ORF editing can also be obtained by other single nucleotide substitutions in the editing locus. In such a NDV V$^-$ mutant a U residue of the editing locus is substituted by C, G or A residue, preferable by a C residue, or a C residue of the editing locus is substituted by a U, G or A residue, preferably by a U residue.

Advantageous examples of such NDV V$^-$ mutants are NDV mutants comprising the nucleotide sequence UCUUUCCC, UUUGUCCC and UUUUCCCC at the editing locus.

A typical example of a NDV mutant according to the invention having 2 mutations at the editing locus comprises the nucleotide sequence GCUUUCCC.

The desired mutations can be introduced into the NDV genome by means of methods generally known in the art for this purpose. In particular, the mutations are introduced by means of site-directed mutagenesis. Such a method is described herein, but is also generally used in the art (Peeters et al., 1999, supra; Current Protocols in Molecular Biology, eds.: F. M. Ausubel et al., Wiley N.Y., 1995 edition, pages 8.5.1.-8.5.9.and Kunkel et al., Methods in Enzymology Vol. 154, 376–382, 1987).

A particular preferred NDV V$^-$ mutant to be used according to the present invention is a NDV mutant as described above which comprises additional attenuating mutations. Such NDV mutants can be derived from any ND vaccine strain. Examples of such suitable NDV vaccine strains present in commercially available ND vaccines are: Clone-30®, La Sota, Hitchner B1, NDW, C2 and AV4, Clone-30® being the preferred vaccine strain.

In another aspect, the present invention provides a live vaccine against ND in birds suitable for in ovo administration, characterised in that the vaccine comprises a NDV V$^-$ mutant as described above, together with a pharmaceutical acceptable carrier.

Typically, such a vaccine comprises doses of 100 µl or less, preferably 50 µl, per egg. The administration of the in ovo vaccine in such small dosages volumes improves the hatchability of the vaccinated embryos.

In a further embodiment of the present invention a live combination vaccines is provided which, in addition to the NDV V$^-$ mutant described above, comprises an embryo-safe vaccine strain of another avian pathogen. The combined administration of more than one vaccine strain is advantageous for economical reasons, because it requires fewer vaccine inoculations in the egg. Moreover, the fewer a needle is introduced into an egg, the less risk of contaminating the eggs exists.

With an embryo-safe vaccine strain is meant a live vaccine strain which, if inoculated into SPF eggs at embryonation day 18, results in the hatchability of the eggs of at least 70%, preferably at least 90%. In particular, the combination vaccine additionally comprises one or more embryo-safe vaccine strains of Marek's disease virus (MDV), infectious bronchitis virus (IBV), infectious bursal disease virus (IBDV), fowl adenovirus (FAV), turkey rhinotracheitis virus (TRTV) or reovirus. Examples of such embryo-safe vaccine strains are the MDV vaccines Ovovac®-HVT and Ovovac®-SB1, the IBDV vaccines Bursamune® and Bursaplex®.

It will be clear that because of the advantageous attenuated properties of the NDV V mutant as shown herein, the live vaccine according to the present invention can also be administered to birds after hatch in a similar way as the live ND vaccines which are routinely used to prevent ND in commercial flocks.

In still a further embodiment of the present invention a vector vaccine is provided which can be used not only for the preparation of a vaccine against infection by a specific NDV, but also against other poultry infectious diseases. For example, a vector vaccine based on a NDV V$^-$ mutant as described above offers the possibility to immunise against other avian pathogens by the expression of antigens of these avian pathogens in infected cells of the immunised host. Such a NDV vector can be obtained by inserting a heterologous nucleic acid sequence encoding a polypeptide heterologous into a non-translated region of the NDV V$^-$ mutant. Non-translated region suitable for this purpose are located between the genomic promoter and the start of the NP gene, and at the NP/P, P/M, M/F, F/HN and HN/L gene junctions. The heterologous nucleic acid sequence may encode an antigen of an avian pathogen such as infectious bursal disease virus, infectious bronchitis virus, Marek's disease virus, avian encephalomyelitis virus, avian reovirus, avian influenza virus, chicken anaemia virus, Salmonella spp., *E.coli*, and Eimeria spp.

The NDV V$^-$ mutant described above also offers the possibility to prepare an inactivated vaccine with advantageous properties for post-hatch administration. An important advantage of such an inactivated vaccine is the high level of protective antibodies of long duration that can be achieved as a result of the high antigenic mass produced by the NDV V$^-$ mutant upon propagation in embryonated eggs or cell culture.

The aim of inactivation of the ND viruses harvested after the propagation step is to eliminate reproduction of the viruses. In general, this can be achieved by chemical or physical means. Chemical inactivation can be effected by treating the viruses with, for example, enzymes, formaldehyde, β-propiolactone, ethylene-imine or a derivative thereof. If necessary, the inactivating compound is neutralised afterwards. Material inactivated with formaldehyde can, for example, be neutralised with thiosulphate or sodium metabisulfite. Physical inactivation can preferably be carried out by subjecting the viruses to energy-rich radiation, such as UV light, X-radiation or γ-radiation. If desired, the pH can be brought back to a value of about 7 after treatment.

A vaccine containing the inactivated ND virus can, for example, comprise one or more of the above-mentioned pharmaceutically acceptable carriers or diluents suited for this purpose.

Preferably, an inactivated vaccine according to the invention comprises one or more compounds with adjuvant activity. Suitable compounds or compositions for this purpose include aluminium hydroxide, -phosphate or -oxide, oil-in-water or water-in-oil emulsion based on, for example a mineral oil, such as Bayol F® or Marcol 52® or a vegetable oil such as vitamin E acetate, and saponins.

The vaccine according to the invention comprises an effective dosage of the NDV V$^-$ mutant as the active component, i.e. an amount of immunising NDV material that will induce immunity in the vaccinated birds against challenge by a virulent ND virus. Immunity is defined herein as the induction of a significant higher level of protection in a population of birds after vaccination compared to an unvaccinated group.

Typically, the live vaccine according to the invention can be administered in a dose of $10^{3.0}$–$10^{8.0}$ embryo infectious dose$_{50}$ (EID$_{50}$) per egg or bird, preferably in a dose ranging from $10^{4.0}$–$10^{7.0}$ EID$_{50}$, in particular $10^{5.0}$–$10^{7.0}$ EID$_{50}$.

Inactivated vaccines may contain the antigenic equivalent of $10^{4.0}$–$10^{9.0}$ EID$_{50}$ per animal, preferably between $10^{6.0}$–$10^{8.0}$ EID$_{50}$ per animal.

Inactivated vaccines are administered parenterally, e.g. intramuscularly or subcutaneously.

Although, the vaccine according to the present invention may be used effectively in chickens, also other poultry such as turkeys, guinea fowl and partridges may be successfully vaccinated with the vaccine.

NDVs have also been described as therapeutic agents in humans, particularly in the treatment of human cancer (Lorence et al., J.Natl Cancer Inst. 80, 1305–1312, 1988; Murray et al., Cancer 52, 856–862, 1983; Reichard et al., J.Surg.Res. 52, 448–453, 1992). Since NDV causes conjunctivitis in humans, a highly attenuated NDV strain is desired for therapy purposes. Therefore, in view of the advantageous properties of the NDV V$^-$ mutant described above, the NDV mutant (if desired, comprising a foreign gene encoding a therapeutic or prophylactic protein) may be used as a therapeutic agent in humans, e.g. in the control of human or animal cancer and AIDS.

EXAMPLES

Example 1

Preparation of a NDV V$^-$ mutant

MATERIALS AND METHODS cDNA synthesis and assembly of full-length clone. Details of these experiments were described by Römer-Oberdörfer et al. (1999, supra). NDV strain Clone-30® (Intervet International B.V., The Netherlands) was purified from 50 ml of allantoic fluid with a titer of $10^{10}$ embryo-infectious doses (EID$_{50}$) per ml. Viral RNA was isolated by guanidinium isothiocynate extraction and subsequent centrifugation through a CsCl cushion. cDNA to genomic RNA was generated by using SuperScript™ II Rnase H Reverse Transcriptase (Gibco). PCR was carried out on 1 μl of the first strand cDNA using the Expand High Fidelity (HF) PCR system (Boehringer Mannheim, Germany). The terminal sequences of the genomic RNA were determined as described by Mundt and Mueller (Virology 209, 209–219, 1995). Then specific oligonucleotides for PCR were deduced to amplify leader and trailer. PCR of these fragments contained an arificially created MluI sites (nt 76 in the noncoding region of NP and nt 15,039 in the noncoding region of L) by mutation of five nucleotides (nt 76, 79, 15,039, 15,041 and 15,042). For construction of a complete NDV antigenome expressing plasmid, the above PCR fragments were cloned in multiple steps between the T7 RNA polymerase promoter and the autocatalytic hepatitis delta virus ribozyme sequence into the SmaI site of plasmid X8dT (Schnell et al., EMBO J. 13, 4195–4203, 1994). The resultant full-length clone is named pflNDV.

Construction of expression plasmids. For the constructuion of NP, P and L expression plasmids open reading frames of NP (nt 122 to 1791), P (nt 1887 to nt 3254) and L (nt 8,381 to 15,051) were cloned into pCite 2a (Novagen). For this purpose, HF-PCR fragments were generated with the respective translation start codon contained in an Ncol or AflIII adapter. These fragments were transferred into pCite 2a vector in the correct open reading frame (Römer-Oberdörfer et al., 1999, supra).

Introduction of mutations into the full-length NDV cDNA. To introduce an attenuating-mutation into the genome of Newcastle Disease Virus (NDV), plasmid pflNDV, expressing the full-length antigenome RNA of the lentogenic Clone-30 NDV vaccine strain was used as a basis. Since NDV edit its P gene mRNA, by inserting non-templated G residues we modified the editing site (UUUUUCCC) by introducing 1, 2, 3 or 6 nucleotide substitutions or deletions or 6 or 12 nucleotides indicated in FIG. 1. PCR was performed with the template pflNDV using the respective primers listed in Table 1. PCR products were then digested by AatII/ApaI and cloned into the same sites of pflNDV. To selectively block expression of the unique C-terminal part of the V protein, a stop codon was introduced into the trans V frame without affecting the P frame. PCR was performed and the product was digested with ApaI and RsrII and ligated into the same site of pflNDV. The region newly introduced into each clone was sequenced to rule out PCR introduced errors. The resultant full-length clones, with nucleotide substitutions or deletions at the editing site, or insertion of a stop codon in the V ORF, were named as shown in FIG. 1.

Generation of recombinant viruses. Approximately 1.5× 10⁶ BSR T7/5 cells stably expressing phage T7 RNA polymerase (Buchholz et al, J. Virology 73, 251–259, 1999) were grown overnight to 90% confluence. Cells were transfected with plasmid mixtures containing 5 μg of pCite-NP, 2.5 μg of pCite-P, 2.5 μg of pCite-L and 10 μg of one of the full-length clones using a mammalian transfection kit (CaPO$_4$ transfection protocol; Stratagene). Three to five days after transfection, supematant was harvested and injected into the allantoic cavity of 9–11 day-old embryonating chicken eggs (200 μl per egg). The presence of virus in the allantoic fluid was determined by haemagglutination (HA) test after 3–4 days of incubation. Virus stocks were prepared after 2–6 passages in embryonated eggs.

RT-PCR. Total RNA from infected BSR T7/5 cells was prepared 36 h after infection using the Rneasy kit (Qiagen). Reverse transcription by avian myeloblastosis virus reverse transcriptase was primed with NDV P-gene specific oligonucleotide P#13 (5'-CCACCCAGGCCACAGACGAAG-3', nucleotides 2676–2196) (SEQ ID NO:45) using 1 μg of total RNA. DNA amlification was done with primer P#13 and P#17 (5'-ATGAATTCAGCTGTTGGA-3', nucleotides 2680–2696) (SEQ ID NO:46) The PCR products were analyzed on I% agarose gels and used directly for sequencing.

Serial passaging of viruses in embryonated SPF eggs. The recombinant NDV V⁻ viruses were serially passed for two to nine times in 9–11 day old embryonated SPF eggs. Inoculated eggs were incubated for 2–5 days at 37° C. Allantoic fluid from each infected egg was first subjected to standard HA test and only HA-positive allantoic fluid was harvested and used for subsequent passage. Virus stocks in each passage were titrated in 9–11 day old embryonated SPF eggs.

TABLE 1

Primers used to introduce mutations into the full-length cDNA clone pflNDV. The nucleotide changes are shown in bold. The nucleotide sequences and nucleotide positions are in accordance with Römer-Oberdörfer et al., J. Gen. Virol. 80, 2987–2995, 1999; EMBL accession no. Y18898)

| | Sequence (5'-3' orientation) | Nucleotide position |
|---|---|---|
| P1: | CCA TGG GCC CTT CTT AGC ATT GGA CG (SEQ ID NO:31) | 2269–2294 |
| PCG12: | CCA TGG GCC CTT TCG AGC ATT GGA CG (SEQ ID NO:32) | 2269–2294 |
| PG2: | CCA TGG GCC CTT TCT AGC ATT GGA CG (SEQ ID NO:33) | 2269–2294 |
| PC4: | CCA TGG GCC CTG TTT AGC ATT GGA CG (SEQ ID NO:34) | 2269–2294 |
| PG5: | CCA TGG GCC CCT TTT AGC ATT GGA CG (SEQ ID NO:35) | 2269–2294 |
| PA: | CCA TGG GCC CTT CGC AGC ATT GGA CG (SEQ ID NO:36) | 2269–2294 |
| PD: | CCA TGG GCC CTT GTC AGC ATT GGA CG (SEQ ID NO:37) | 2269–2294 |
| PR: | CCA TGG GCC CTT GCG AGC ATT GGA CG (SEQ ID NO:38) | 2269–2294 |
| PRR: | CCA TGG GCC CCG GCG AGC ATT GGA CG (SEQ ID NO:39) | 2269–2294 |
| Δ6: | CCA TGG GCC --- --- AGC ATT GGA CG (SEQ ID NO:40) | 2269–2294 |
| Δ12: | CCA TGG GCC --- --- --- --- GGA CGA TTT ATT GCT GAG (SEQ ID NO:41) | 2256–2294 |
| Vstop: | AAG GGC CCA TGG TCT AGC CCC CAA GAG (SEQ ID NO:42) | 2283–2309 |
| FWP#4: | GCT CCT CGC GGC TCA GAC TCG (SEQ ID NO:43) | 151–171 |
| RP#20: | CCC GGG AAT CTT CTC TGG CGC (SEQ ID NO:44) | 3764–3784 |

Anti-V peptide antibody production. In order to detect V protein expression in infected cells, a serum specifically recognizing the C-terminus of V protein is essential, since P, V, and W proteins are amino-coterminal. For this purpose, we selected a potential antigenic sequence in the unique C-terminus of V protein and synthesized a peptide comprising the 16 C-terminus amino acids of V protein (amino acids position 224–239). Five mg of the peptide was conjugated to a carrier protein-keyhole limpet hemocyanin (KLH). Two rabbits were immunized with the KLH-conjugated peptide and boosted twice after 2 and 4 weeks. Blood samples were collected before the first injection (pre-immune) and 2 and 3 months later.

Immunoblotting. For virus purification, 9- to 11-day old embryonated SPF chicken eggs were infected and allantoic fluid was collected 3–4 days post-infection. Virus in the allantoic fluid was then purified and concentrated by centrifugation through a 20% sucrose cushion in a Beckman SW28 rotor at 21,000 rpm for 90 min. The pellet was resuspended and mixed with protein sample buffer to disrupt the virions. Viral proteins from purified virions were then resolved by sodium dodecyl sulfate-polyacrylamide gel electrophoresis, transferred to PVDF membranes (Millipore), and incubated with the anti-V peptide serum specific for the C-terminal 16 amino acids 6f the V protein of NDV, Clone-30 strain, or monoclonal antibody (MAb) specific for NDV NP-protein. Membranes were then incubated with peroxidase-conjugated goat anti-rabbit or anti-mouse immunoglobulin-G. Proteins were visualized after incubation with peroxidase substrate (Vector).

Immunofluorescence analysis for V-protein expression. For the analysis of viral protein expression, BSR-T7 cells were infected at a multiplicity of infection (moi) of ~10 with various passage levels of NDV V$^-$ or the parent virus and incubated for 1–2 days. Infected cells were fixed with cold ethanol (96%) for I hr at room temperature. After washing three times with PBS cells were incubated with an anti-V-peptide rabbit serum (serum collected after 3 months of first immunization) for 1 hr at 37° C. Parallelly infected cells were incubated with MAbs reacting with NDV F or NP protein or with a polyclonal chicken serum recognising various NDV proteins. Cells were washed and stained with FITC conjugated anti-rabbit, anti-chicken or anti-mouse antibody and examined by fluorescence microscopy.

Determination of P-gene mRNA editing frequency. Total RNA isolated from cells infected with FINDV and serial passages of NDV V$^-$ mutant P1 is subjected to reverse transcription using oligo(dT) primer to amplify only mRNAs. PCR was then performed with primers P#17 (NDV V-EcoRI 2680 5'-ATG AAT TCA GCT GTT GGA-3') (SEQ ID NO:46) and P#13 (NDV P+2176 5'-CCA CCC AGG CCA CAG ACG AAG-3') (SEQ ID NO:45). The PCR fragment was digested with EcoRV and SalI and ligated into the same site of pSKT7T vector. Cloned plasmids were sequenced from independent colonies and examined for the presence or absences of insertion of a non-templated G residue(s) at the editing site (Table 2).

RESULTS

Recovery of P-gene mRNA Editing-defective NDVs From cDNA Clones.

In order to disrupt the conserved P-gene mRNA editing or selectively block expression of the unique C-terminal part of V protein, the modifications shown in FIG. 1 were carried out on the full-length cDNA clone (pflNDV) of NDV, Clone-30 strain. Each modified full-length cDNA clone, together with three support plasmids expressing NDV NP, P, and L proteins, was transfected into BSR-T7/5 cells. Transfection experiments were also performed with the unmodified full-length cDNA, pflNDV, to compare rescue efficiencies. After 3–5 days of incubation, supernatants were harvested and transfected cells were subjected to immunofluorescence (IF) staining using anti-F MAb. At least 20–50 IF-positive cells were detected in all of the transfection experiments involving pflNDV or modified full-length clones, showing that there was genome replication and expression of viral proteins in cell culture.

Embryonated SPF chicken eggs, which have been known for long as the best substrates for propagation of lentogenic NDVs (Nagai et al., Virology 72, 494–508, 1976), were then inoculated with transfection supernatants. After 3–4 days of incubation, allantoic fluid samples were harvested and subjected to a HA test. HA was detected in some eggs inoculated with the supernatant from cells transfected with the pflNDV. However, 1 to 2 extra egg passages were required for the modified viruses containing one or two nucleotide substitutions at the editing site (NDV-P1, NDV-PG2, NDV-PC4, NDV-PG5 and NDV-PCG12) to be detected using the HA test.

Surprisingly, infectious virus was not detected in the allantoic fluid of embryonated eggs inoculated with transfections supernatants obtained from deletion mutants (NDV-Δ6 and NDV-Δ12), mutants possessing three or more nucleotide substitutions (NDV-PA, NDV-PD, NDV-PR, NDV-PRR) or the mutant lacking the unique C-terminal part of V protein (NDV-Vstop). In spite of three repeated rescue experiments and four successive egg passages in each experiment, we were unable to detect infectious virus in the allantoic fluid of embryonated eggs.

Mutants, for which recovery was possible, were then serially passed 2 to 6 times in 9- to 11-day old embryonated eggs.

Expression of V protein. To determine the presence or absence of V protein expression, BSR-T7 cells were infected with various mutants (NDV-P1, NDV-PG2, NDV-C4, NDV-PG5 and NDV-PCG12) or the parental virus and processed for immunofluorescence analysis or RNA isolation. Using a chicken anti-NDV serum or MAbs reacting with NDV F or NP, the level and pattern of fluorescence in cells infected either with one of the mutants or the parent virus was indistinguishable. In contrast, the anti-V peptide serum reacted with high fluorescence intensity only with cells infected with the FINDV. Similar concentration of the serum revealed a specific but very weak fluorescence signal, which was comparable within the mutants and higher passage of NDV P1 (passage levels 5–9), indicating similar low levels of V expression in all the examined mutants. This indicated that, in spite of the interruption of the U-stretch at the editing locus, RNA editing and hence V protein expression is not completely abolished in the mutant viruses, including passage level 6 of P1 that previously showed no V ORF mRNA among 39 mRNA clones examined. The mutant NDV P1 was then chosen for further analysis.

Figure 2:
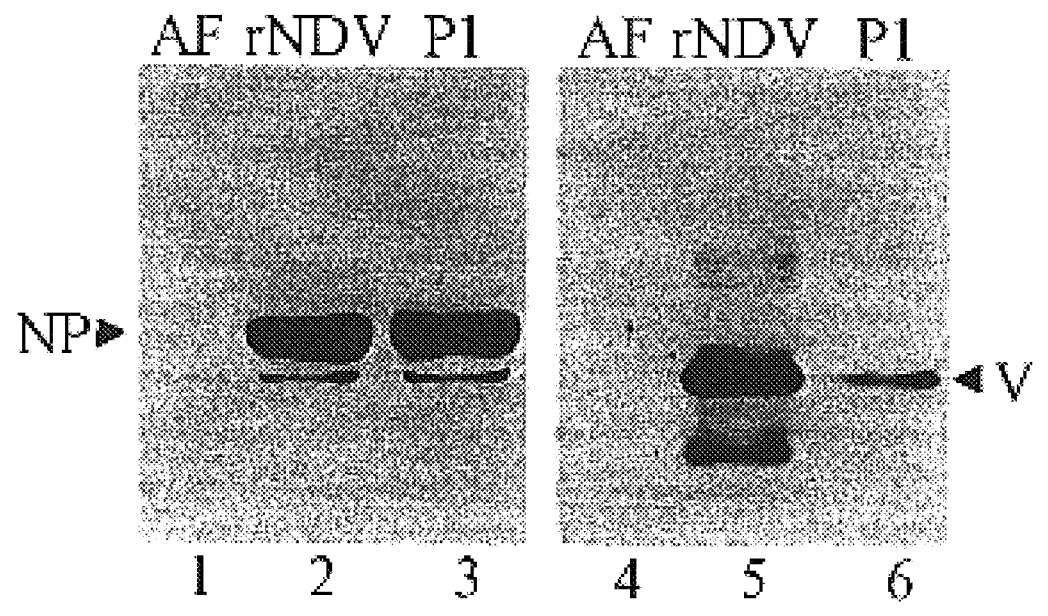

V protein is a structural component of NDV, therefore it was of interest to determine whether the low level V expression in infected cells would lead to low level incorporation of V into virions. Thus, NDV P1 virions purified and concentrated through 20% sucrose were subjected to immunoblotting experiments. Using NP specific MAb, which is reactive with the NP protein of both viruses with equal sensitivity, it was possible to standardize the amount of protein loaded into the gel (FIG. 2). Although comparable amounts of the parent virus and NDV V$^-$ mutant P1 proteins were subjected to the Western blot analysis, the V protein of NDV V$^-$ mutant was considerably less than that of the parent virus, demonstrating low level V protein incorporation into NDV V$^-$ virions. Analysis of diluted samples by Western blot revealed that the V protein content of NDV V$^-$ virions was approximately 20-fold lower than that of the parent virus.

The sequence around the editing locus of the NDV V$^-$ P-gene mRNA was then determined from a total of 319 independent colonies of plasmids derived from passage levels 5 to 9 (Table 2). For comparison, a total of 41 independent colonies were sequenced for F1NDV and 28 out 41 (68.3%) of the sequenced plasmids encoded the unedited version of P-protein. Plasmids encoding the V-protein with insertion of one non-templated G residue were 12 out of 41 (29.3%). Only one plasmid out of 41 possessed an insertion of two non-templated G residues (Table 2). In contrast, out of total 319 sequenced independent colonies of NDV V$^-$ mutant P1, only four plasmids contained an insertion of non-templated G residue(s) leading to V-ORF. The V encoding plasmids at passage level 6, 8 and 9 have a single G insertion, whereas the plasmid at the passage level 7 possessed an insertion of four G residues, which also would result in V protein expression. Taken together, these results show that the substitution made at the RNA editing site did not completely block P-gene mRNA editing, but dramatically reduced the RNA editing frequency. Compared to the parent virus, the NDV V$^-$ virus edits its P-gene mRNA at 10–20 fold lower frequency and hence synthesizes V protein at a corresponding low level.

TABLE 2

Determination of P-gene mRNA editing frequency of NDV V$^-$ mutant P1

| Virus | Passage Level | Total No. of colonies | Expressed proteins | | |
|---|---|---|---|---|---|
| | | | P | V | W |
| F1-NDV | 3 | 41 | 28 (68.3%) | 12 (29.3%) | 1 (2.4%) |
| NDV V$^-$ | 5 | 56 | 56 (100%) | 0 | 0 |
| NDV V$^-$ | 6 | 72 | 71 (98.6%) | 1 (1.4%) | 0 |
| NDV V$^-$ | 7 | 42 | 41 (97.6%) | 1 (2.4%) | 0 |
| NDV V$^-$ | 8 | 105 | 104 (99%) | 1 (~1%) | 0 |
| NDV V$^-$ | 9 | 44 | 43 (97.7%) | 1 (2.3%) | 0 |

Example 2

In Vivo Experiments With the NDV V$^-$ Mutant: Vaccination of SPF Chicken Embryos

MATERIALS AND METHODS

Virus titration in embryonating eggs. Serial 10-fold dilution of the recombinant virus was performed and two groups of 11 day-old embryonating eggs were inoculated with the serial dilutions. An HA test was carried out on one group of inoculated eggs after 4 days of incubation and the titer, expressed as 50% embryo-infectious dose (EID$_{50}$) was calculated using the method of Reed and Muench (Am.J.Hyg. 27, 493–497, 1938). The other group of inoculated eggs was observed daily for embryo mortality and the 50% embryo-lethal dose (ELD$_{50}$) was also determined using the same method.

In ovo vaccination and challenge. Eighteen-day-old fertilized eggs from SPF chicken were inoculated through a hole punched at the blunt end of the egg. Using a 23G needle, 0.1 ml of the virus dilution or negative allantoic fluid was injected just below the air membrane. The rate of hatchability was recorded and all chickens were observed daily for general health condition. At 14 days of age, all chickens were weighed and bleed. Serum samples were examined for the presence/absence of antibodies to NDV in the standard NDV haemagglutination inhibition test. At 14 days of age (~17 days after vaccination) all animals were challenged intramuscularly with the virulent NDV, strain Herts. Chickens were observed daily for a period of 10 days for the occurrence of clinical signs of disease or mortality.

RESULTS

NDV V$^-$ Pathogenicity. NDV isolates vary in their virulence to embryonating eggs as well as to chickens. The degree of virulence of a given NDV isolate can be measured by assessing the pathogenicity of the virus in vivo. One of these methods involves calculating the mean death time (MDT) for 10–12 day-old chicken embryos infected with one minimum lethal dose of the virus. The MDT for some well-characterized NDV strains ranges from 48 hr for velogenic and some mesogenic strains to 160 hr for lentogenic strains (most vaccine strains). For the purpose of determining the mean embryo-lethal dose of the NDV V$^-$ mutants, serial 10-fold virus dilution was inoculated to 11 day-old embryonating eggs and incubated for 7 days. Surprisingly, no specific embryo mortality was detected during the observation in the groups inoculated with NDV P1 and NDV PC4 (Table 3), showing that these NDV V$^-$ mutants are safe for chicken embryos even when inoculated at 11 days of age and at higher dose (Table 3). To our knowledge, these are the first examples of NDV strains that do not cause embyo mortality. A second group of mutants consisting of PG2, PG5 and PCG12 cause low level of embryo mortality under similar conditions, but still dramatically attenuated in pathogenicity for chicken embryos. The difference between the EID$_{50}$ and ELD$_{50}$ of these mutants is at least 4.8 log$_{10}$, compared to 0.3 log$_{10}$, for the parent virus, showing that they are attenuated at least 30,000 fold more than their parent virus (Table 4).

TABLE 3

Determination of embryo mortality after inoculation of NDV P1 or NDV PC4 into 11 day-old embryonated SPF chicken eggs during 7 days of incubation

| | Embryo mortality (No. dead/No inoculated) | | |
|---|---|---|---|
| Virus dilution (log$_{10}$) | Parent NDV | NDV P1 mutant | NDV PC4 mutant |
| 1 | 8/8 | 0/8 | 0/8 |
| 2 | 8/8 | 0/8 | 0/8 |
| 3 | 8/8 | 0/8 | 0/7 |
| 4 | 8/8 | 0/7 | 0/8 |
| 5 | 8/8 | 0/8 | 0/8 |
| 6 | 8/8 | 0/8 | 0/8 |
| 7 | 3/6 | 0/7 | 0/8 |
| 8 | 2/6 | 0/8 | 0/8 |
| 9 | 0/6 | 0/5 | — |
| 10 | 0/6 | — | — |

TABLE 4

Difference between the EID$_{50}$ and ELD$_{50}$ of NDV mutants

| Mutants | EID$_{50}$ | ELD$_{50}$ | Difference |
|---|---|---|---|
| NDV P1 | 6.7 | 0 | 6.7 |
| NDV PC4 | 7.4 | 0 | 7.4 |
| NDV PG2 | 8.4 | 3.4 | 5.0 |
| NDV PG5 | 9.1 | 3.5 | 5.6 |
| NDV PCG12 | 8.2 | 3.4 | 4.8 |
| Parent NDV | 9.2 | 8.9 | 0.3 |

NDV V$^-$ hatchability when applied in ovo. Currently there is no live ND vaccine that can be applied in ovo, mainly due to high embryo mortality and very low hatchability even with the highly attenuated NDV strains. Since the NDV V⁻ mutants PI and PC4 were found non-pathogenic for embryos when applied at the embryonation day of 11, an embryo vaccination experiment was performed on 18 day-old embryonating eggs using NDV V⁻ mutant P1 and NDW (Poulvac NDW®, a commercially available post-hatching live vaccine, Fort Dodge USA). Hatchability was found to reach up to 93% (28 out of 30) for NDV V⁻ compared to 96% (29 out of 30) for the control group (Table 5). The least hatchability (23%) was obtained for the group of eggs inoculated with the NDW, one of the most attenuated live vaccines. This result shows that the NDV V⁻ mutant does not significantly affect hatchability.

NDV V protects chicken against a lethal challenge. At two weeks of age, all chickens hatched from in ovo inoculated eggs were bleed, weighed and challenged with Herts strain of NDV by intramuscular inoculation (Table 5). Chickens vaccinated as embryos with NDV V⁻ developed high antibody levels and gained a mean weight of 131 gm compared to 85 gm for the NDW inoculated animals and 141 gm for the control animals. Interestingly, more than 95% of NDV V vaccinated animals were protected against challenge exposure, whereas all non-vaccinated chickens died. These data show that NDV V⁻ mutant is safe and efficacious when applied to 18 day-old embryonating eggs originated from SPF chickens.

TABLE 5

Hatchability and protection of chickens inoculated with recombinant NDV V⁻ mutant P1 at 18 day of embryonation against lethal NDV challenge

| Virus | Dose log₁₀ EID₅₀/egg | Hatch-ability | Mean weight at 2 weeks (gm) | Mean HI titre at two weeks[A] | Survival after Challenge[B] |
|---|---|---|---|---|---|
| NDV V⁻(a) | 3.5 | 22/30 (73%) | 133 | 4.0 ± 1.1 | 19/20 (95%) |
| NDV V⁻(b) | 4.3 | 28/30 (93%) | 135 | 4.8 ± 1.0 | 20/20 (100%) |
| NDV V⁻(c) | 5.4 | 21/30 (70%) | 125 | 5.4 ± 1.2 | 19/19 (100%) |
| NDW | 5.1 | 7/30 (23%) | 85 | 7.5 ± 0.9 | Nd |
| Control | 0 | 29/30 (96%) | 141 | 0.7 ± 0.5 | 0/20 (0%) |

[A]Hemagglutination-inhibition (HI) titre (2log) at two weeks of age.
[B]Chickens were challenged with Herts strain of NDV 10⁵·⁵ ELD₅₀/chicken intramuscularly.
Nd: not done Example 3

In Vivo Experiments With the NDV V⁻ Mutant P1: Vaccination of Commercial Chicken Embryos

MATERIALS AND METHODS

In ovo vaccination and challenge. This experiment in commericial chicken embryos, possessing maternally derived antibodies, was essentially carried out as described for in ovo experiment in SPF chicken embryos. In short, a total of 120 eighteen-day old fertilized commercial chicken eggs were assigned to four groups of each 30 eggs. NDV V⁻ was applied in ovo in three different doses to three different groups. One group of 30 eggs was inoculated with negative allantoic fluid. At 14 days of age (~17 days after vaccination) all animals were challenged intramuscularly with virulent NDV, strain Herts. Chickens were observed daily for a period of 10 days for the occurrence of clinical signs of disease or mortality. Just before challenge, blood samples were collected from all vaccinated and control chickens individually. The sera were examined for antibodies against NDV by HI test.

RESULTS

Hatchability and weight gain in NDV V⁻ vaccinated chickens. Similar to the results obtained for SPF chicken eggs, hatchability of embryonated commercial chicken eggs was not affected by in-ovo administration of NDV V⁻ (Table 6). All hatched chickens were healthy in all groups before challenge. More over, the weight gain of all groups of chickens vaccinated with NDV V⁻ was comparable to that of the negative control group, demonstrating the safety of NDV V⁻ when administerd in-ovo to 18 day-old embryonated commercial chicken eggs.

Seroconversion and protection against a lethal challenge. The level of antibody response and protection for chickens vaccinated as embryos with NDV V⁻ is shown in Table 6. The group that received the highest dose had a mean HI titre of 1.8 and 85% of the chickens in this group were protected against the challenge. The ability of NDV V⁻ to break through the presumably high level of maternal antibody at the time of application and confer protection to 85% of the chickens is remarkable. As the level of protection is dose dependent, a slightly higher dose is expected to protect more than 90% of vaccinated chickens.

TABLE 6

Hatchability and protection of chickens inoculated with recombinant NDV V⁻ mutant P1 at 18 day of embryonation against lethal NDV challenge

| | In-ovo vaccination | | | Mean weight | | |
|---|---|---|---|---|---|---|
| Group | Vaccine | log₁₀ EID₅₀/egg | Hatchability amount/total | HI titre (2log) against NDV (a) | at 2 weeks of age (g) | Survival after challenge (b) |
| 1 | NDV V⁻ (a) | 3.7 | 29/30 (96%) | 1.4 ± 1.0 | 439 | 7/20 (35%) |
| 2 | NDV V⁻ (b) | 4.5 | 29/30 (96%) | 1.5 ± 0.9 | 413 | 15/20 (75%) |
| 3 | NDV V⁻ (c) | 5.7 | 27/30 (90%) | 1.8 ± 1.1 | 438 | 17/20 (85%) |
| 4 | Control | — | 29/30 (96%) | 1.2 ± 0.9 | 440 | 4/20 (20%) |

(a) Haemagglutination-inhibition (HI) titre (2log) at two weeks of age.
(b) Chickens were challenged with Herts strain of NDV at a dose of 10⁵·⁵ ELD₅₀/chicken intramuscularly.

LEGEND TO THE FIGURE

FIG. 1

Introduction of mutations into the editing locus of the P gene of Newcastle disease virus genome. A schematic representation of the NDV gene order is shown in the negative-strand genomic RNA. Sequences around the editing site (position 2274–2300) are presented in a positive sense. The modifications are shown in boxes. Amino acid changes as a result of the various modifications were shown in bold. The nucleotide sequences and nucleotide positions are in accordance with Romer-Oberdorfer et al., J. Gen. Virol. 80, 2987–2995, 1999; EMBL accession no. Y18898) (SEQ ID NOS:1–30).

FIG. 2

NP and V proteins of sucrose purified recombinant viruses. Virions in the allantoic fluid of infected embryonated eggs were purified by centrifugation through 20% sucrose and viral proteins were subjected to immunoblotting analysis. The volumes loaded on the gel were normalized according to the NP content. Samples were loaded in duplicate and blots were incubated with anti-NP MAb (lanes 1–3) or with anti-V peptide serum (lanes 4–6). AF: allantoic fluid from non-infected embryonated eggs; P1: NDV V$^-$ mutant P1; rNDV: the parent FlNDV virus.

---

We claim:

1. An isolated Newcastle disease virus (NDV) mutant that expresses its V protein at a reduced level (NDV V⁻), wherein
the mutant is phenotypically V protein positive and ≦6% of its phosphoprotein (P) gene derived mRNAs in infected cells encode V ORF; and
the mutant comprises a nucleotide substitution at positions 3 or 4 of an editing locus.

2. The NDV mutant according to claim 1, wherein ≦3% of its P-gene derived mRNAs in infected cells V ORF.

3. The NDV mutant according to claim 2, wherein ≦1% of its P-gene derived mRNAs in infected cells encode V ORF.

4. The NDV mutant according to claim 1, wherein an editing locus UUU UUC CC (genome RNA sense) of the P-gene mRNA comprises a mutation to reduce editing.

5. The isolated NDV mutant according to claim 1, wherein the mutation is a silent mutation.

6. The isolated NDV mutant according to claim 1, wherein the mutation comprises one or two nucleotide substitutions.

7. The isolated NDV mutant according to claim 6, wherein the mutation comprises one nucleotide.

8. The NDV mutant according to claim 1, wherein the nucleotide sequence of the editing locus of the NDV mutant is UUC UUC CC or UUUGUCCC.

9. The isolated NDV mutant according to claim 1, wherein the NDV mutant comprises additional attenuating mutations.

10. The isolated NDV mutant according to claim 1, wherein the mutant further comprises a heterologous gene encoding an antigen of an avian pathogen.

11. An inactivated vaccine against Newcastle disease in birds, comprising:
an inactivated isolated NDV mutant according to claim 1,
a pharmaceutically acceptable carrier and
an adjuvant.

12. A method for making a vaccine for protecting birds against Newcastle disease, comprising:
combining the isolated NDV mutant of claim 1 with a pharmaceutically acceptable carrier.

13. A live vaccine against Newcastle disease in birds, comprising:
the isolated NDV mutant according to claim 1, and
a pharmaceutically acceptable carrier.

14. The live vaccine according to claim 13, wherein the vaccine comprises $10^{3.0}$ to $10^{8.0}$ embryo infectious dose$_{50}$ (EID$_{50}$) of the isolated NDV mutant in a dosage volume of 100 μl or less.

15. The live vaccine according to claim 14, wherein the vaccine comprises $10^{3.0}$ to $10^{8.0}$ embryo infectious dose$_{50}$ (EID$_{50}$) of the isolated NDV mutant in a dosage volume of 50 μl.

16. The live vaccine according to claim 13, wherein the vaccine further comprises an embryo-safe vaccine strain of another avian pathogen.

17. A method for protecting birds against Newcastle disease, comprising:
administering a vaccine according to claim 13 to the birds via the in ovo route.

* * * * *